US006646232B2

(12) United States Patent
Richards et al.

(10) Patent No.: US 6,646,232 B2
(45) Date of Patent: *Nov. 11, 2003

(54) FAIL SAFE DEVICE FOR INFANT-SUPPORT APPARATUS

(75) Inventors: John H. Richards, Warrington, PA (US); Robert M. McDonough, Hatfield, PA (US)

(73) Assignee: Hill-Rom Services, Inc., Batesville, IN (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/295,349

(22) Filed: Nov. 15, 2002

(65) Prior Publication Data

US 2003/0066824 A1 Apr. 10, 2003

Related U.S. Application Data

(63) Continuation of application No. 09/838,789, filed on Apr. 20, 2001, now Pat. No. 6,483,080.

(60) Provisional application No. 60/199,103, filed on Apr. 21, 2000.

(51) Int. Cl.$^7$ .............................. H05B 3/50; A61F 7/00; A61G 11/00

(52) U.S. Cl. ........................ 219/385; 219/402; 219/399; 219/530; 219/536

(58) Field of Search .......................... 49/388, 399, 400, 49/402, 580, 536, 540; 600/22

(56) References Cited

U.S. PATENT DOCUMENTS

| | | | | | |
|---|---|---|---|---|---|
| 2,648,327 | A | * | 5/1953 | Gibbon | 600/22 |
| 3,937,923 | A | * | 2/1976 | Smith | 219/536 |
| 4,121,571 | A | | 10/1978 | Pickering | |
| 4,506,140 | A | | 3/1985 | Armstrong | |
| 5,057,657 | A | | 10/1991 | Skulic | |
| 5,285,519 | A | | 2/1994 | Barsky et al. | |
| 5,352,869 | A | | 10/1994 | Barsky | |
| 5,486,205 | A | * | 1/1996 | Cornell et al. | 219/530 |
| 5,707,006 | A | * | 1/1998 | Skulic | 219/543 |
| 5,957,830 | A | | 9/1999 | Skulic | |
| 6,024,694 | A | | 2/2000 | Goldberg et al. | |
| 6,036,633 | A | | 3/2000 | Hodge | |

FOREIGN PATENT DOCUMENTS

| | | |
|---|---|---|
| EP | 0 862 901 | 9/1998 |
| EP | 0 933 075 | 8/1999 |

* cited by examiner

*Primary Examiner*—Joseph Pelham
(74) *Attorney, Agent, or Firm*—Barnes & Thornburg

(57) ABSTRACT

An infant-support heater assembly having a heater element a radiator associated with the heater element and a sensing element in contact with at least a portion of the radiator. The sensing element is separate from the heater element.

17 Claims, 5 Drawing Sheets

FAIL SAFE DEVICE FOR INFANT-SUPPORT APPARATUS

RELATED APPLICATION

The present application is a continuation of co-pending U.S. Utility application Ser. No. 09/838,789, filed Apr. 20, 2001 (Proposed U.S. Pat. No. 6,483,080, proposed to be issued Nov. 19, 2002) which claims the benefit of U.S. Provisional Patent Application Serial No. 60/199,103, filed Apr. 21, 2000, the complete disclosures of which are hereby expressly incorporated by reference.

BACKGROUND AND SUMMARY

The present invention relates to infant-support apparatus or incubators which have air circulation systems provided with air warmers, and, more particularly, to the provision of such a system with a fail safe device for the air warmer.

It is well known in the infant care industry to provide incubators with air circulation systems for controlling the environment within which an infant resides. Such an infant-support apparatus is shown, for example, in U.S. Pat. No. 6,024,694 to Goldberg, et al., the disclosure of which is herein expressly incorporated by reference. Typically, the environment is established by a canopy structure placed over a platform upon which the infant rests. Air is drawn into the environment by the air system and, typically, it is heated and moistened to provide a desired and controlled environment. To reduce the $CO_2$ level in the environment, a certain amount of the air is removed from the enclosure and air is drawn in from the room in which the infant resides. The control of the temperature of the air is very important and, in some cases, critical to the well being of the infant. Typically, the air is heated to the desired level by a heat exchanger of the type shown, for example, in the U.S. Pat. No. 5,707,006 to Skulic, ("the Skulic '006 patent") issued Jan. 13, 1998, the subject matter of which is incorporated herein by reference. The Skulic '006 patent shows a heat radiator for heating the air circulating through an incubator. The radiator has a plurality of radially extending fins carried or mounted on a heater cartridge. The heater of the present invention, however, provides an improvement over the heater disclosed in the Skulic '006 patent. The improvement is a fail safe device for such a heater.

In accordance with the present invention, the air warmer or air heater comprises a heater element, a plurality of air-contacting fins associated with the heater element, and a sensing element in contact with at least a portion of the fins. The sensing element is separate from the heater element. In embodiments of the present invention, the heater element is an elongated element or heating cartridge with a proximal end and a distal end. The plurality of fins are spaced apart along the heater element. The sensing element extends longitudinally alongside and separated from the heater element to contact the fins.

In an illustrative embodiment, a primary temperature sensor is associated with the heater element, and is located at the distal end of the heater element. Then, the fail safe device comprises a separate sensing element in contact with at least a portion of the fins, and a control system for the assembly responsive to the primary sensor and the separate sensing element. In such an embodiment, the separate sensing element is a metal rod, such as an aluminum rod, spaced apart from the heating element and extending through aligned openings disposed through the fins. The sensing element is in heat transfer contact with the fins such that convective heat transfer between the sensing element and fins is facilitated so that the sensing element generates a signal indicative of the temperature of the fins when the fins are present. This elongated metal rod has a proximal end and a distal end, and a heat sensor is located at a proximal end of the metal rod to establish the temperature of the fins in contact with the rod. It will be appreciated that this second sensing element will detect if a service person has cleaned but failed to reinstall the fin assembly on the heater element as radiant heat absorbed by the sensing element from the heater element will not be dissapated through transfer to the missing fin assembly.

An illustrative embodiment comprises a separate heat sensor in contact with at least a portion of the fins of an air warmer to provide a separate indication of the temperature to which the fins are heated. The output of this second sensor is usable to control the heater system of the incubator. If the temperature of the sensing element is excessive or in some manner not within specified predetermined limits, the control system may provide alarm signals to the caregivers, and if the heat is excessive, shut down the heating system to avoid injury to the infant.

The control system for the heater system may shut down the power to the heater element in the event the separate heat sensor reads a temperature in excess of a preset limit or in the event the difference between the temperature read by the primary sensor and the separate sensor is too great.

In illustrative embodiments, the heater element and the separate heat sensor comprise upstanding, post-like structures which are configured to be received in a central bore of a longitudinally extending hub of the fin assembly from which the fins radiate and in a laterally spaced bore through a portion of the hub and the fins. The fin assembly is lowered vertically downwardly on the upstanding heater element and heat sensor to be held in place by gravity. For heat transfer, the heater element and sensor are in sliding contact with the fin assembly.

Additional features and advantages of the device will become apparent to those skilled in the art upon consideration of the following detailed descriptions exemplifying the best mode of carrying out the device as presently perceived.

BRIEF DESCRIPTION OF THE DRAWINGS

The illustrative device will be described hereinafter with reference to the attached drawings which are given as non-limiting examples only, in which.

Corresponding reference characters indicate corresponding parts throughout the several views. The exemplification set out herein illustrates an embodiment of the apparatus and such exemplification is not to be construed as limiting the scope of this disclosure in any manner.

DETAILED DESCRIPTION OF THE DRAWINGS

The present disclosure contemplates that an infant-support like an incubator or warmer will include a control system that will react to a variety of sensors to control a heater assembly 2 that is designed to warm an infant. (See FIG. 1.) One of such sensors will be a fail safe sensor described in detail herein, i.e., a sensor which detects the temperature of heat transfer members which contact and heat the air that warms the infant. In the following disclosure, reference is made to a primary temperature sensor which is associated with the heater assembly. Though the illustrative embodiment shows one temperature sensor which provides control for the heater cartridge, it is contemplated that several such temperature sensors may be used.

Figure 1:
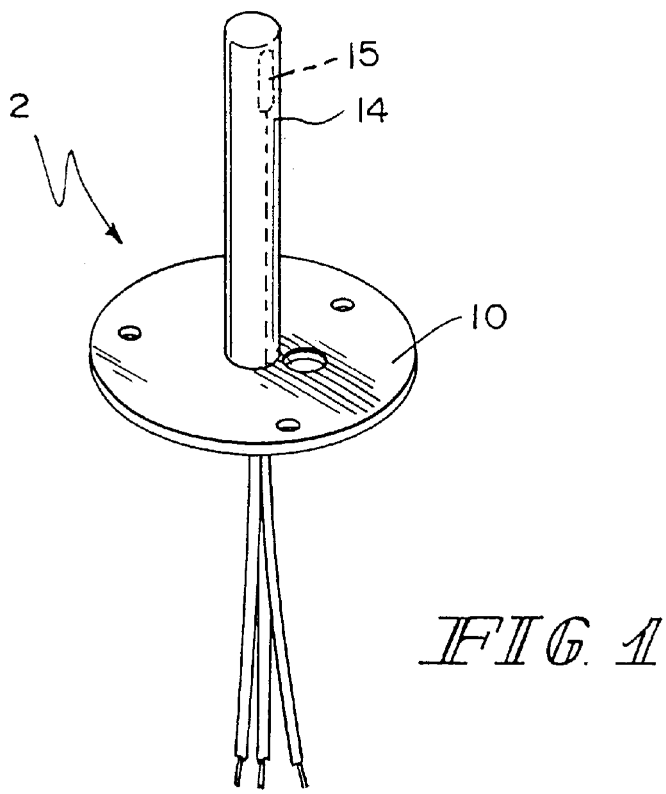
FIG. 1 is a perspective view of a heating cartridge configured for an infant-support apparatus.
Figure 2:
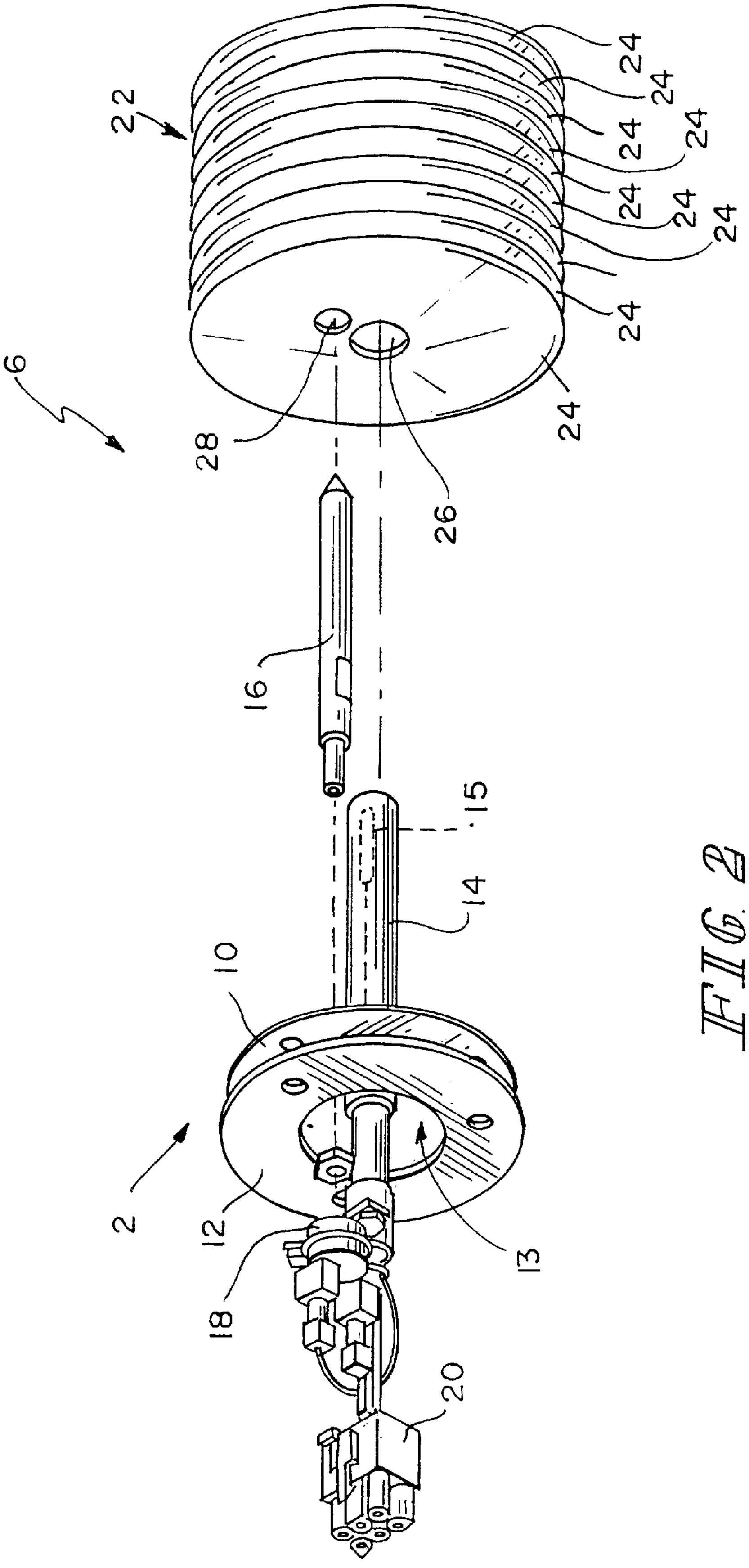
FIG. 2 is an exploded perspective view of a fail safe assembly including the heating cartridge from FIG. 1.

Referring specifically to the drawings, heater assembly 2 of fail safe device 6 provides a mounting plate 10 and a heater cartridge 14 extending through the center of the mounting plate 10, as shown in FIG. 1. (See also FIG. 2.) Heater cartridge 14 includes a thermocouple 15 that monitors the temperature of heater cartridge 14. A gasket 12 having a hole 13 disposed therethrough, as shown in FIG. 2, is placed adjacent mounting plate 10, and is positioned between mounting plate 10 and base plate 30 within chamber 46 of platform tub 44, as discussed further herein below. Extending adjacent, but spaced apart from, heater cartridge 14 is a heat sensor pipe or rod 16 which is illustratively formed from aluminum to serve as a sensor or sensing element. A thermostat 18 is mounted at the base (proximal end) of the sensing element 16. Thermostat 18 is connected to appropriate wiring so as to control energization of heater cartridge 14. An electrical connector 20 which receives wires from heater cartridge 14 and thermostat 18 is provided, as also shown in FIG. 2.

Figure 3:
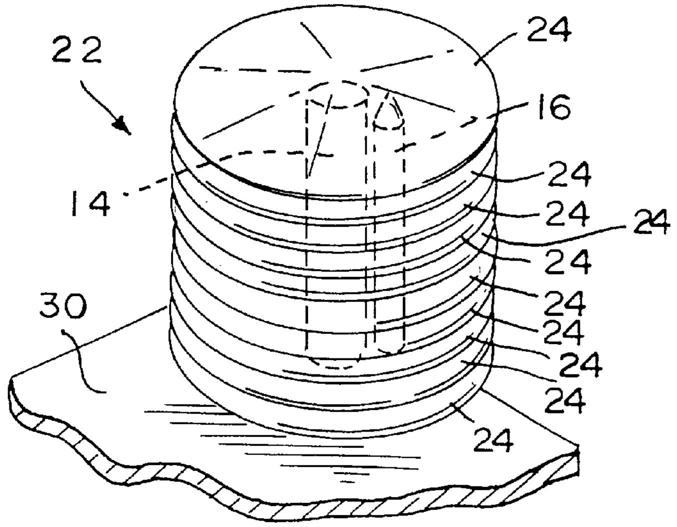
FIG. 3 is perspective view of the fail safe assembly of FIG. 2.

A removable radiator 22, as shown in FIGS. 2 and 3, is formed with a plurality of generally circular radially extending heat transfer members or fins 24. A central bore 26 is provided in the radiator to receive heater cartridge 14. An adjacent bore 28 is also provided through fins 24 to receive the aluminum metal sensing element 16. While the aforementioned Skulic '006 patent shows the radiator held to the plate by a bushing 20, the radiator 22 of the present disclosure is held in place on heater cartridge 14 and sensing element 16 by gravity alone. That is, the fits between the heater cartridge 14 and the sensing element 16 and their respective bores 26 and 28 are sliding fits. When radiator 22 is removed, cleaned and replaced, it is merely placed down over the upwardly extending heater cartridge 14 and sensing element 16.

The radiator 22 of the illustrated embodiment is shown as a cylindrically shaped fin assembly for receiving the heater cartridge 14 and for receiving the sensing element 16. It is contemplated that radiator 22 may have a variety of shapes and structures to provide a plurality of metal fins or other structures that are associated with the heater cartridge 14, which heats the fins. It is further contemplated that sensing element 16 may take several forms to be in contact with at least a portion of the fins.

The fail safe device 6 of the present disclosure also contemplates that the output of the sensing element 16 will be fed through the control circuitry and utilized to provide inputs for the heater control. When heater cartridge 14 or radiator 22 are showing excessive heat, for example, the control system will respond by providing an alarm to the caregiver and/or by shutting down or reducing the energy supplied to the heater cartridge 14.

Figure 4:
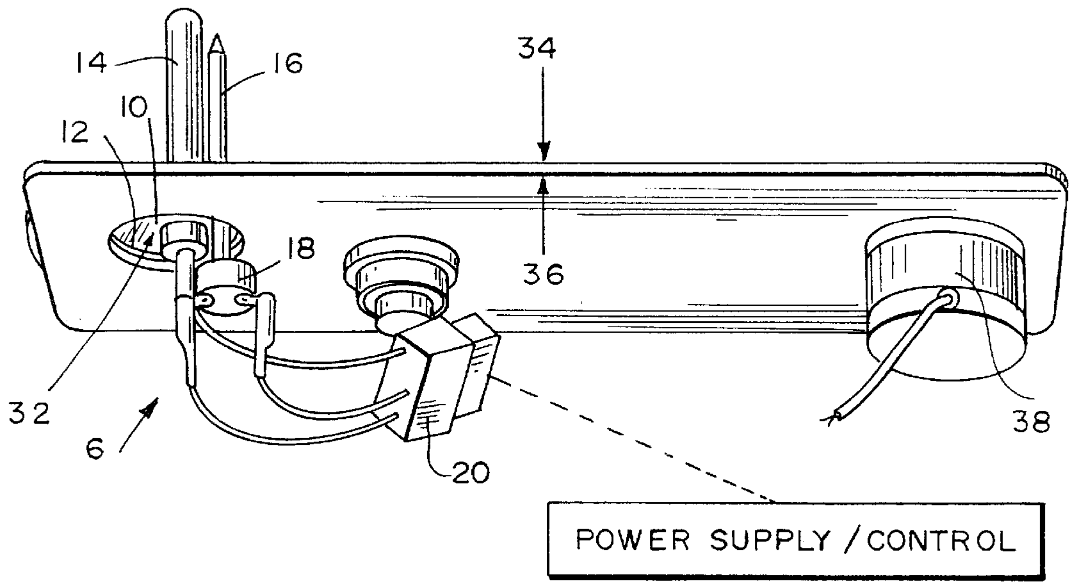
FIG. 4 is a perspective view of the fail safe assembly of FIG. 2 coupled to a portion of the air circulation system of the infant-support apparatus.

As shown in FIG. 4, fail safe device 6 extends through a hole 32, which is disposed through base plate 30. The mounting plate 10, heater cartridge 14, gasket 12 and sensing element 16 are above or extend through hole 32 and are located on the upper side 34 of base plate 30. The thermostat 18, electrical connector 20, and other wiring are located on the lower side 36 of base plate 30. Also shown in FIG. 4 is fan motor 38 of fan 42. (See also FIGS. 5 and 6.)

It is contemplated that electrical connector 20 is coupled to power supply/controller assembly 21. The power supply portion will provide the power necessary to heat heater cartridge 14, and the controller portion will process signals from thermocouple 15 and sensing element 16 to monitor and adjust the amount of power supplied to heater cartridge 14. In one embodiment it is contemplated that thermocouple 15 serves as a primary temperature sensor that allows the controller portion of assembly 21 to control the power supplied to heater cartridge 14 for maintaining a desired temperature. In addition, thermocouple 15 provides temperature readings to the controller which can respond if the temperature is too high by providing an alarm to the caregiver and/or by shutting down or reducing the power supplied to the heater cartridge 14. In this embodiment, sensing element 16 serves as a redundancy to thermocouple 15, to the extent that thermostat 18 can substantially reduce or shut down the power supplied to the heater cartridge 14. It is appreciated that the function of sensing element 16 will be used if thermocouple 15 fails.

Figure 5:
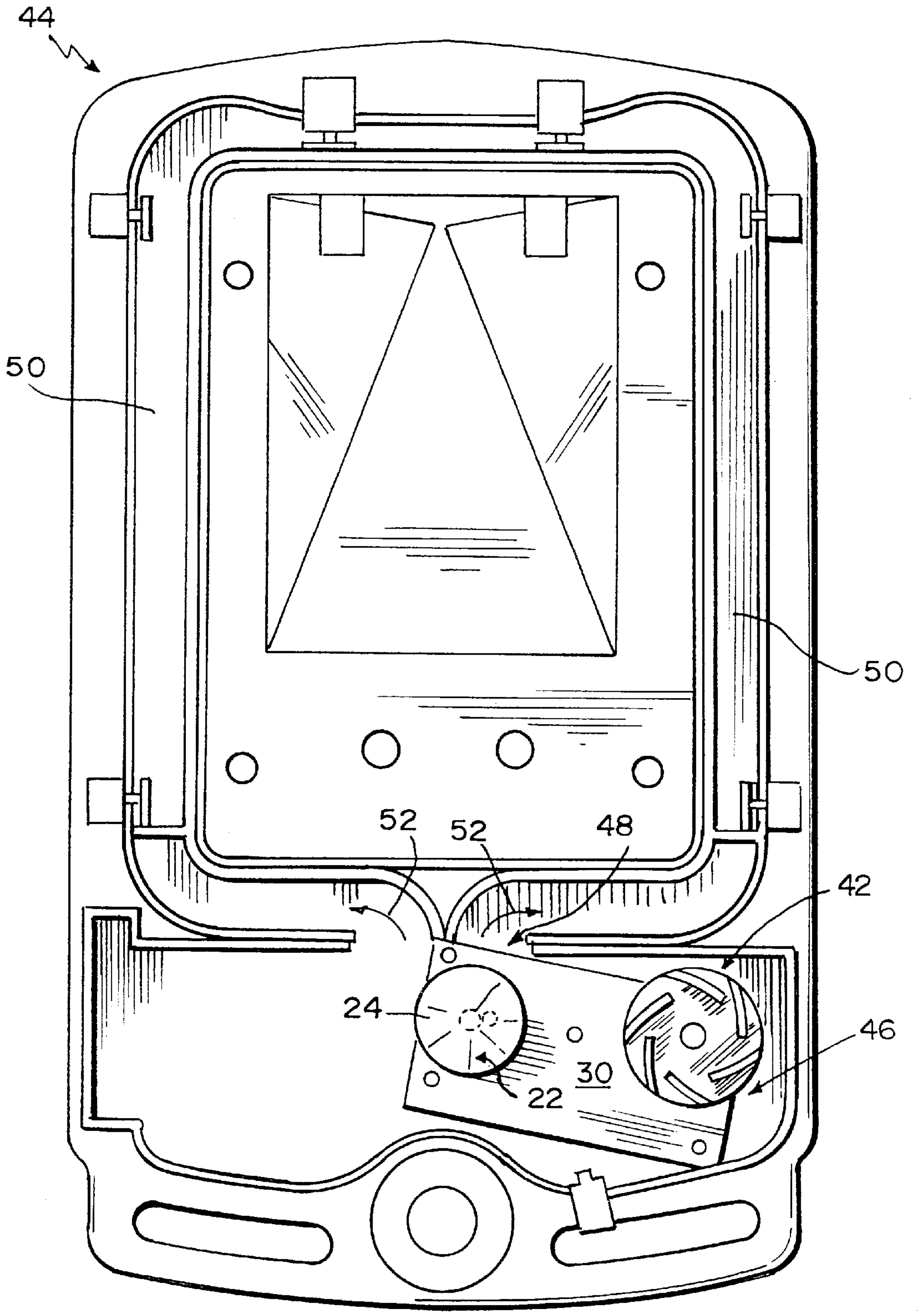
FIG. 5 is a top plan view of the platform tub portion of the infant-support apparatus showing the air circulation system.
Figure 6:
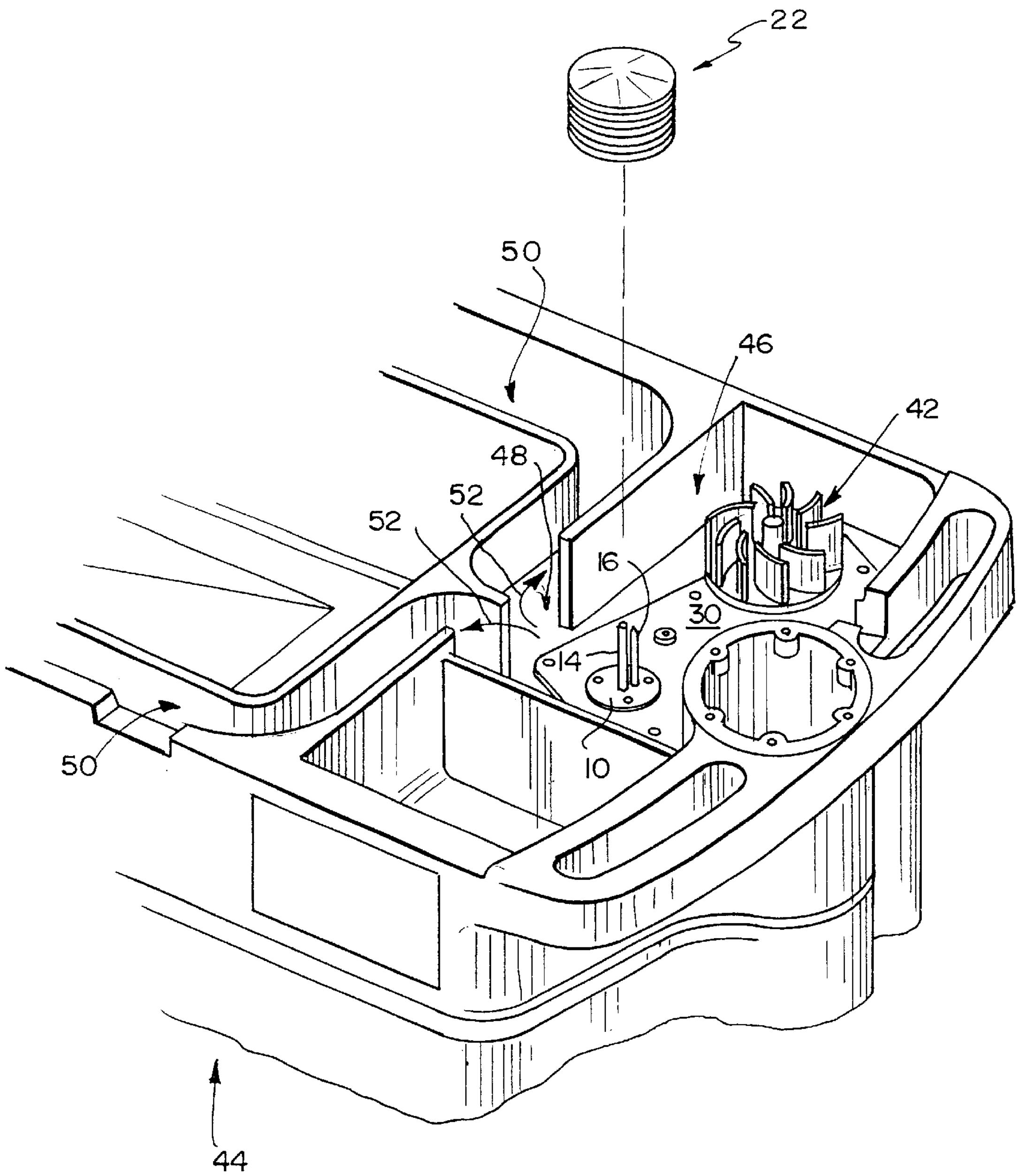
FIG. 6 is a partial perspective view of the tub platform of the patient-support apparatus of FIG. 5 showing the air circulation system including the fail safe assembly with the radiator removed.

Base plate 30 along with fail safe device 6 and fan 42 are configured to be positioned within chamber 46 of platform tub 44. It is contemplated that fail safe device 6 be part of an overall air or fluid circulation system that circulates air from fan 42 through fins 24 of radiator 22, through opening 48, and into air flow channels 50, as shown in FIGS. 5 and 6. It is contemplated that an air filter (not shown) can be positioned to lie above base plate 30 through which air is drawn by fan 48. The directional movement of the air flow is indicated by reference numeral 52. The air flow is moved through channels 50 and out through vent slots (not shown) adjacent a platform (not shown) upon which an infant rests. It is appreciated that platform tub 44 is for use with either an incubator, warmer or other similar infant-support apparatus that uses a convection or similar type heat system.

As depicted in FIG. 6, radiator 22 is removable from heater cartridge 14 and sensing element 16. As previously discussed, radiator 22, illustratively, may be removed with it only being secured to device 2 by gravity. Once radiator 22 is removed, a caregiver, or other personnel, has access to heater cartridge 14 and sensing element 16 to clean or repair same, as well as clean or repair radiator 22. The caregiver can then replace radiator 22 over heater cartridge 14 and sensing member 16, as previously discussed. If the caregiver fails to replace radiator 22 properly, the heat produced from heater cartridge 14 will not have the same ability to dissipate as it did with radiator 22 when attached thereto. Accordingly, sensing element 16 along with thermostat 18 will detect an increase temperature of heater cartridge 14. The heat, being at such an elevated level, will cause the control system to respond by providing an alarm to the caregiver and/or shutting down or reducing the energy supplied to heater cartridge 14.

Although the foregoing embodiments have been described, one skilled in the art can easily ascertain the essential characteristics of the device, and various changes and modifications may be made to adapt the various uses and characteristics without departing from the spirit and scope of this application, as described by the claims which follow.

What is claimed is:

1. An infant incubator heater assembly comprising:

a mounting plate adapted for attachment to a base of an incubator;

a heat radiator having a plurality of radially extending fins; and a cartridge heater extending through said heat radiator in heat transfer relationship with said heat radiator the heat radiator being held on the cartridge heater by gravity without the presence of a bushing therebetween.

2. The infant incubator heater assembly of claim 1 comprising a sensing element in contact with at least a portion of the heat radiator and wherein the sensing element is separate from the cartridge heater.

3. The infant incubator heater assembly of claim 2, in which the cartridge heater element is elongated with a proximal end and a distal end, the plurality of fins being spaced along the cartridge heater, the sensing element extending longitudinally alongside the cartridge heater to contact the fins.

4. The infant incubator heater assembly of claim 3, wherein the sensing element is a primary temperature sensor associated with the cartridge heater and further comprising a separate temperature-sensing element in contact with at least a portion of the fins; and a control system associated with the assembly which is responsive to the primary sensor and the separate sensing element.

5. The heater assembly of claim 4, in which the primary temperature sensor is associated with the distal end of the cartridge heater and the separate temperature-sensing element is elongated and spaced apart from the heater element to contact the fins.

6. The heater assembly of claim 5, in which the separate sensing element is an elongated metallic rod having a proximal end and a distal end, and a heat sensor at the proximal end of the metallic rod to establish the temperature of the fins in contact with the rod.

7. The heater assembly of claim 6, in which the fins are provided with aligned openings for receiving the rod.

8. An incubator heater assembly comprising:

a compartment;

a heater assembly positioned in said compartment and having:

(a) a mounting plate adapted for attachment to a wall of said compartment, (b) a heat radiator and having a plurality of radially extending fins, and (c) a cartridge heater extending through said heat radiator in heat transfer relationship with said heat radiator, the heat radiator being held on the cartridge heater by gravity without the presence of a bushing therebetween;

a fan for forcing air into said compartment for passage of said air past said fins of said heat radiator; and means for supplying power to said cartridge heater.

9. The incubator heater assembly of claim 8 comprising a sensing element in contact with at least a portion of the heat radiator and wherein the sensing element is separate from the cartridge heater.

10. The infant incubator heater assembly of claim 9, in which the cartridge heater element is elongated with a proximal end and a distal end, the plurality of fins being spaced along the cartridge heater, the sensing element extending longitudinally alongside the cartridge heater to contact the fins.

11. The infant incubator heater assembly of claim 10 wherein the sensing element is a primary temperature sensor associated with the cartridge heater and further comprising a separate temperature-sensing element in contact with at least a portion of the fins; and a control system associated with the assembly which is responsive to the primary sensor and the separate sensing element.

12. The heater assembly of claim 11, in which the primary temperature sensor is associated with the distal end of the cartridge heater and the separate temperature-sensing element is elongated and spaced apart from the heater element to contact the fins.

13. The heater assembly of claim 12, in which the separate sensing element is an elongated metallic rod having a proximal end and a distal end, and a heat sensor at the proximal end of the metallic rod to establish the temperature of the fins in contact with the rod.

14. The heater assembly of claim 13, in which the fins are provided with aligned openings for receiving the rod.

15. An infant-support heater assembly comprising:

a heater element;

a plurality of air-contacting fins associated with the heater element to heat the air in contact with the fins;

wherein the fin assembly is held on the heater element by gravity.

16. The infant-support heater assembly of claim 15 wherein the heater element is a cartridge heater.

17. The infant-support heater assembly of claim 15 and further comprising a mounting plate adapted for attachment to a base of an incubator.

* * * * *